United States Patent [19]

Sommer et al.

[11] Patent Number: 4,675,411

[45] Date of Patent: Jun. 23, 1987

[54] CHEMICAL AGENTS

[75] Inventors: Harold Z. Sommer, Havre de Grace; Jacob I. Miller, Rockdale, both of Md.

[73] Assignee: The United States of America as represented by the Secretary of the Army, Washington, D.C.

[21] Appl. No.: 563,628

[22] Filed: Jun. 10, 1966

[51] Int. Cl.⁴ .................. C07D 213/63; C07D 213/72
[52] U.S. Cl. .................................................. 546/292
[58] Field of Search ............... 260/296; 167/33 D, 46, 167/47; 546/292; 514/346

[56] References Cited

U.S. PATENT DOCUMENTS 2,512,732  6/1950  Aeschlimann et al. ............. 546/292

OTHER PUBLICATIONS

Jones, R. Jr. et al., J. Org. Chem., vol. 22, pp. 783-786, 1957.

Primary Examiner—John F. Terapane
Assistant Examiner—Virginia B. Caress
Attorney, Agent, or Firm—Anthony T. Lane; Robert P. Gibson; Harold H. Card, Jr.

[57] ABSTRACT

Novel toxic compounds being useful as chemical warfare agents in various munitions.

The compound having the following structure:

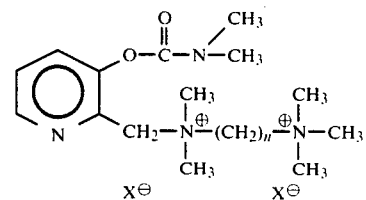

where n is an integer from 6 to 16 and where X is halide, sulfate, nitrate, hydrogenoxalate or perchlorate forming a stable salt.

9 Claims, No Drawings

CHEMICAL AGENTS

This invention relates to the synthesis of new toxic chemical compounds which are useful as chemical warfare agents. More particularly, our invention is concerned with novel compounds produced by quaternizing 2-dimethylaminomethyl-3-dimethylcarbamoxypyridine with ω-halo-alkyl trisubstituted ammonium halide.

The chemical agents of our invention act mostly on the peripheral autonomic cholinergic nervous system which includes the motor nerves, all preganglionic parasympathetic fibers. The transmission of impulses along a nerve or from nerve fibers to muscle fibers or secretory cells, or from one nerve fiber to another across synapses in ganglia is thought to involve chemical changes, either directly or as the source of potential differences. The nerve action current results from a redistribution of diffusible ions between the center of the nerve and the periphery, taking place successively along the nerve fiber. This redistribution of ions may be under the control of chemical agencies. Our chemical agents interfere with the normal process of neuromuscular impulse transmission and thus disrupt the propagation of impulses along the motor nerve fibers entering the muscles. We have also found these compounds to be extremely toxic at relatively low dose levels in various animals.

The object of this invention is to synthesize new lethal agents in substantial yields wherein said products are well 1-(N,N-Dimethylamino)-12-[N-(3-dimethylcarbamoxy-2-pyridylmethyl-N-methylamino]dodecane dimethobromide.

1-(N,N-Dimethylamino)-13-[N-(3-dimethylcarbamoxy-2-pyridylmethyl-N-methylamino]tridecane dimethobromide.

1-(N,N-Dimethylamino)-14-[N-(3-dimethylcarbamoxy-2-pyridylmethyl)-N-methylamino]tetradecane dimethobromide.

1-(N,N-Dimethylamino)-15-[N-(3-dimethylcarbamoxy-2-pyridylmethyl)-N-methylamino]pentadecane dimethobromide.

1-(N,N-Dimethylamino)-16-[N-(3-dimethylcarbamoxy-2-pyridylmethyl)-N-methylamino]hexadecane dimethobromide.

We have shown a preferred compound in which the anion is limited to the halogen moiety, in particular the bromide, since the bromoalkanes are readily available and are good quaternizing agents. In general, however, it is only necessary that the anions merely have to meet the requirement of being capable of forming a stable salt with the quaternary nitrogen. Thus, the halogen ions can be exchanged with other anions of a relatively strong monovalent or polyvalent acids by conventional methods. For example, if X is a bromide in the final product, a solution of the compound can be treated with a basic ion exchange resin or mixed with silver oxide and subsequently the desired acid is added to the quaternary hydroxide solution. In like manner, the sulfate, nitrate, hydrogenoxalate, perchlorate salts may be prepared. Representative examples of these additional monovalent or polyvalent end products are:

1-(N,N-Dimethylamino)-10-[N-(3-dimethylcarbamoxy-2-pyridylmethyl)-N-methylamino]decane dimethosulfate.

1-(N,N-Dimethylamino)-10-[N-(3-dimethylcarbamoxy-2-pyridylmethyl)-N-methylamino]decane dimethonitrate.

1-(N,N-Dimethylamino)-10-[N-(3-dimethylcarbamoxy-2-pyridylmethyl)-N-methylamino]decane dimethohydrogenoxalate.

1-(N,N-Dimethylamino)-10-[N-(3-dimethylcarbamoxy-2-pyridylmethyl)-N-methylamino]decane dimethoperchlorate.

We claim:

1. A new chemical toxic agent of the formula:

$$\text{Pyridine ring with substituents: } 3\text{-O-C(=O)-N(CH}_3\text{)}_2 \text{ and } 2\text{-CH}_2\text{-}\overset{\oplus}{\text{N}}(\text{CH}_3)_2\text{-(CH}_2)_n\text{-}\overset{\oplus}{\text{N}}(\text{CH}_3)_2\text{-CH}_3 \cdot 2X^{\ominus}$$

wherein n is 6 to 16 carbon atoms and X represents one equivalent of an anion forming a stable salt with the quaternary nitrogen.

2. The salts of claim 1 wherein X is selected from the group of anions consisting of halide, sulfate, hydrogenoxalate, nitrate, and perchlorate.

3. The compound 1-(N,N-Dimethylamino)-7-[N-(3-dimethylcarbamoxy-2-pyridylmethyl)-N-methylamino]heptane dimethobromide.

4. The compound 1-(N,N-Dimethylamino)-8-[N-(3-dimethylcarbamoxy-2-pyridylmethyl)-N-methylamino]octane dimethobromide.

5. The compound 1-(N,N-Dimethylamino)-9-[N-(3-dimethylcarbamoxy-2-pyridylmethyl)-N-methylamino]nonane dimethobromide.

6. The compound 1-(N,N-Dimethylamino)-10-[N-(3-dimethylcarbamoxy-2-pyridylmethyl)-N-methylamino]decane dimethobromide.

7. The compound 1-(N,N-Dimethylamino)-11-[N-(3-dimethylcarbamoxy-2-pyridylmethyl)-N-methylamino]hendecane dimethobromide.

8. The compound 1-(N,N-Dimethylamino)-12-[N-(3-dimethylcarbamoxy-2-pyridylmethyl)-N-methylamino]dodecane dimethobromide.

9. The compound 1-(N,N-Dimethylamino)-13-[N-(3-dimethylcarbamoxy-2-pyridylmethyl)-N-methylamino]tridecane dimethobromide.

* * * * *